United States Patent [19]

Pollet et al.

[11] 4,038,075

[45] July 26, 1977

[54] DEVELOPMENT OF PHOTOGRAPHIC SILVER HALIDE MATERIAL

[75] Inventors: Robert Joseph Pollet, Vremde; Francis Jeanne Sels, Kontich; Camille Angelina Vandeputte, Mortsel, all of Belgium

[73] Assignee: AGFA-GEVAERT N.V., Mortsel, Belgium

[21] Appl. No.: 648,721

[22] Filed: Jan. 13, 1976

[30] Foreign Application Priority Data

Jan. 22, 1975 United Kingdom ............... 2866/75

[51] Int. Cl.² .................. G03C 7/00; G03C 7/16; G03C 5/30

[52] U.S. Cl. .................................. 96/22; 96/55; 96/66.3

[58] Field of Search .............. 96/66 R, 55, 66.3, 107, 96/221

[56] References Cited

U.S. PATENT DOCUMENTS

| | | | |
|---|---|---|---|
| 2,828,265 | 3/1958 | Van Strien | 96/107 |
| 3,038,805 | 6/1962 | Dann et al. | 96/107 |
| 3,046,129 | 7/1962 | Graham et al. | 96/107 |
| 3,046,134 | 7/1962 | Dann et al. | 96/107 |
| 3,518,085 | 6/1970 | Milton et al. | 96/66.3 |
| 3,523,797 | 8/1970 | Willems et al. | 96/66.3 |
| 3,574,628 | 4/1971 | Jones | 96/107 |
| B 417,498 | 3/1976 | Pollet et al. | 96/66.3 |

*Primary Examiner*—Mary F. Kelley
*Attorney, Agent, or Firm*—A. W. Breiner

[57] ABSTRACT

A method is described of developing a photographic silver halide element containing developable silver halide by means of a silver halide developing composition, comprising as development activator a derivative of a polyethylene glycol or a $C_1$-$C_5$ monoalkyl ether thereof corresponding to the formula:

$$R_1O(CH_2CH_2O)_nX-A-Y-R_2$$

wherein
$R_1$ is hydrogen, $C_1$-$C_5$ alkyl or the group $X-A-Y-R_2$
$n$ is an integer of at least 4
$X$ is CO, $SO_2$, CONH or, when $R_1$ is $X-A-Y-R_2$ may be a chemical monovalent bond,
$A$ is alkylene or arylene,
$Y$ is a sulphur or selenium atom, and
$R_2$ is an alkyl group.

10 Claims, No Drawings

DEVELOPMENT OF PHOTOGRAPHIC SILVER HALIDE MATERIAL

The present invention relates to silver halide developers comprising development activating polyethylene glycol derivatives and to the use of thest developers for the development of exposed silver halide elements.

It is known to increase the sensitivity of photographic emulsions by addition of chemical sensitizers e.g. sulphur-containing compounds, reducing agents and salts of gold or other noble metals or combinations of these compounds. Such chemical sensitizers are believed to react with the silver halide to form, on the surface of the silver halide, minute amounts of silver sulphide or of silver or of other noble metals which increases the sensitivity of the silver halide emulsion. This kind of chemical sensitization, however, reaches a limit beyond which further addition of sensitizer or further digestion with the sensitizer merely increases the fog of the emulsion with constant or decreasing speed.

As is known in the art, further increasing of the speed of the photographic reproduction system can be effected by the presence during development of alkylene oxide polymers, e.g. polyoxyethylene compounds, thioether compounds and/or onium or polyonium compounds of the ammonium, phosphonium or sulphonium type. These compounds sensitize the emulsion by development acceleration and may be used either in the emulsion or the developer.

We have now found that development of exposed silver halide emulsions can be activated by the use of developers containing derivatives of polyethylene glycols with average molecular weights of at least 200 or of mono $C_1$–$C_5$ alkyl ethers thereof, wherein the said derivatives correspond to the following general formula:

$$R_1O(CH_2CH_2O)_n X-A-Y-R_2$$

wherein $R_1$ is hydrogen, $C_1$–$C_5$ alkyl e.g. methyl or the group $X-A-Y-R_2$ $n$ is an integer of at least 4, X is CO, $SO_2$, CONH or, when $R_1$ is $X-A-Y-R_2$, may be a chemical monovalent bond, A is alkylene, preferably $C_1$–$C_5$ alkylene, or arylene e.g. phenylene, Y is S or Se, and $R_2$ is alkyl, preferably $C_1$–$C_5$ alkyl which may carry substituents e.g. hydroxyalkyl and carboxyalkyl.

The present invention thus provides a method for the development of a photographic element containing developable silver halide by means of a silver halide developing composition containing a polyethylene glycol derivative corresponding to the above general formula.

The present invention also provides a silver halide developing composition containing a silver halide developing agent and a polyethylene glycol derivative corresponding to the above general formula.

The derivatives of polyethylene glycols or monoalkyl ethers thereof corresponding to the above general formula can be prepared, as is illustrated by the preparations hereinafter, by partial or complete conversion of the terminal hydroxyl group(s) of the polyethylene glycol or monoalkyl ether. Many of these polyethylene glycols and monoalkyl ethers are commercially available generally in the form of mixtures of varying molecular weight. For the preparation of derivatives corresponding to the above general formula, the polyethylene glycols or monoalkyl ethers thereof have an average molecular weight of at least 200.

Representative examples of polyethylene glycol derivatives corresponding to the above general formula are given in the following preparations:

PREPARATION 1:

$H_3CSCH_2CH_2COO(CH_2CH_2O)_nOCCH_2CH_2SCH_3$ 150 g of polyethylene glycol (average molecular weight 1500) in 900 ml of benzene and 27.7 g of methylthiopropionyl chloride in 150 ml of benzene were mixed whereupon, at a temperature below 10° C, 20.2 g of triethylamine in 100 ml of benzene were added dropwise. The mixture was left standing at room temperature for 15 days and the triethylamine hydrochloride precipitate was filtered off by suction. The filtrate was evaporated. Yield: 171 g.

Preparation 2:

10 g of polyethylene glycol (average molecular weight 200) in 100 ml of benzene and 23.3 g of p-methylselenobenzoyl chloride in 150 ml of benzene were mixed whereupon, at a temperature below 20° C, 10.1 g of triethylamine in 60 ml of benzene were added dropwise. The mixture was left standing at room temperature for 5 days and the triethylamine hydrochloride precipitate was filtered off by suction. The filtrate was evaporated. Yield: 29 g.

Preparation 3:

150 g of polyethylene glycol (average molecular weight 1500) in 1000 ml of benzene and 37.3 g of p-methylthiobenzoyl chloride in 300 ml of benzene were mixed whereupon, 20.2 g of triethylamine in 100 ml of benzene were added dropwise at room temperature. The mixture was left standing at room temperature for 20 days and the precipitate of triethylamine hydrochloride was filtered off. The filtrate was evaporated. Yield: 180 g.

PREPARATION 4

Preparation 3 was repeated with the difference that polyethylene glycol of average molecular weight 200 was used. Yield: 50 g.

Preparation 5:

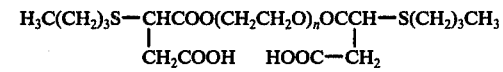

A mixture of 75 g of polyethylene glycol (average molecular weight 1500) and 18.8 g of butylthiosuccinic anhydride in 600 ml of toluene was boiled for 10 hours and then concentrated by evaporation. Yield: 94 g.

PREPARATION 6:
$H_5C_2SCH_2CH_2NHCOO(CH_2CH_2O)_n OCNHCH_2CH_2SC_2H_5$

A mixture of 150 g of polyethylene glycol (mol weight 1500) and 28.9 g of ethylthioethylisocyanate in 1000 ml of benzene was boiled for 6 hours and then concentrated by evaporation. The residue was extracted with hot hexane and dried. Yield: 126 g.

PREPARATION 7 :

Preparation 6 was repeated with the difference that the reaction occurred with 60 g of polyethylene glycol (molecular weight 400) and 39.3 g of ethylthioethylisocyanate in 500 ml of toluene. Yield: 98 g.

PREPARATION 8 :

Preparation 6 was repeated with the difference that the reaction occurred with 200 g of polyethylene glycol (molecular weight 4000) and 14.4 g of ethylthioethylisocyanate in 600 ml of toluene. Yield: 210 g.

PREPARATION 9 :
$H_3CO(CH_2CH_2O)_n OCNHCH_2CH_2-SC_2H_5$

This preparation is analogous to preparation 6 with the difference that 75 g of methoxy polyethylene glycol (molecular weight 750) and 14.4 g of ethylthioethylisocyanate in 500 ml of toluene were used. Yield: 87 g.

PREPARATION 10:
$HOCH_2CH_2S(CH_2CH_2O)_n CH_2CH_2SCH_2CH_2OH$

To a solution of 127.5 g of the bis-toluene sulphonic acid ester of polyethylene glycol (molecular weight 200) in 600 ml of ethanol, a solution of 11.5 g of sodium and 39 g of mercaptoethanol in 400 ml of ethanol was added at 40° C. The mixture was boiled for 8 hous and then concentrated by evaporation. The residue was taken up in acetone and the precipitate of sodium toluene sulphonate was filtered off by suction.

The filtrate was concentrated by evaporation. Yield: 63 g.

PREPARATION 11 :

Preparation 10 was repeated with the difference that 177.5 g of the bis-toluene sulphonic acid ester of polyethylene glycol (molecular weight 400) were used. Yield: 125 g.

If desired, the polyethylene glycol derivative of the present invention can be treated with various alkylating agents e.g. the esters of an alcohol and a strong acid such as methyl or ethyl esters of sulphuric acid, phosphoric acid, hydrochloric acid, hydrobromic acid, hydroiodic acid, benzene sulphonic acid, p-toluene sulphonic acid, etc. to convert at least one thioether S-atom into a sulphonium atom. In general, it suffices to merely heat the polyethylene glycol derivative with the alkylating agent. By the presence of the ternarized sulphonium atoms, improved solubility in water or various water-miscible solvents can be obtained.

The compounds corresponding to the above general formula can be used in developing compositions comprising black-and-white developing agents e.g. hydroquinone, hydroquinone/ 1-phenyl-3-pyrazolidinone, hydroquinone/p-monomethylaminophenol sulphate or colour developing agents more particularly aromatic primary amino colour developing agents e.g. p-phenylene diamine colour developing agents. They are particularly suitable for use in colour developing solutions.

The development accelerating compounds can be utilized in various concentrations, depending upon the effects desired, the particular silver halide emulsions employed, the thickness of the emulsion layers, the concentration of silver halides in the emulsions, the concentration of developing agents in the developers, the pH of the developers etc. The optimum amount for any given compound can be determined for any particular emulsion or developer by running a series of tests in which the quantity is varied over a certain range.

In general, useful results are obtained when the concentration of the thioether compound in the developer is from about 50 mg to about 10 g per liter. The activity of the developer will obviously depend upon the temperature of development, which may be room temperature or elevated temperature e.g. above 30° C, upon the duration of development and the like.

The developers can also contain conventional addenda e.g. alkaline salts (sodium carbonate, potassium carbonate, sodium hydroxide, sodium metaborate, etc.) restraining agents e.g. potassium bromide, hydroxylamine and derivatives, alkali metal sulphites e.g. sodium sulphite, calcium sequestering compounds e.g. ethylene diamine tetraacetic acid and salts thereof and sodium pyrophosphate, development accelerating onium compounds, e.g. of the type described in U.S. Pat. No. 3,682,634, etc. fog-inhibitors e.g. the alkalisoluble compounds of British Patent Application, No. 43 517/71.

The silver halide emulsions which are developed according to the present invention comprise as light-sensitive salt, silver bromide, silver iodide, silver chloride or mixed silver halides e.g. silver chlorobromiode, silver chlorobromiodide or silver bromoiodide.

The emulsions can be chemically sensitized by any of the accepted procedures. The emulsions can be digested with naturally active gelatin or with sulphur-containing compounds e.g. allyl isothiocyanate, allyl thiourea or sodium thiosulphate. The emulsion can also be digested in the presence of reducing agents e.g. the tin compounds described in Belgian Patent Specifications Nos. 493,464 and 568,687, the iminoaminomethane sulphinic acid compounds described in United Kingdom Patent Specification No. 789,823, polyamines e.g. diethylene triamine, spermine and bis(β-aminoethyl)sulphide. They can further be digested in the presence of noble metal compounds such as ruthenium, rhodium, palladium, iridium, platinum and gold compounds as described by R. Koslowsky, Z. Wiss. Phot. 46, 65–72 (1951). Representative compounds are ammonium chloropalladate, potassium chloroplatinate, sodium chloropalladite, potassium chloroaurite, potassium aurithiocyanate, potassium chloroaurate, gold(III) chloride, gold(I) sulphide, etc.

The emulsions can comprise emulsion-stabilizers and fog-inhibiting compounds e.g. the mercury compounds such as those described in Belgian Patent Specifications Nos. 524,121 and 677,337 and in published Dutch Patent Application No. 67/15932, organic sulphur-containing compounds that form insoluble silver salts with silver ions, heterocyclic nitrogen-containing thioxo compounds or derivatives thereof, e.g. benzothiazoline-2-thione, 1-phenyl-2-tetrazoline-5-thione and 2-ethoxycarbonylthio-5-amino-thiadiazole, the compounds described in Belgian Patent Specifications Nos. 571,916 and 571,917, thiazolinium compounds of the type described in Product Licensing Index, December 1971 issue, p. 90–91, benzothiazolium compounds e.g. 2,3-dimethyl-5-methoxycarbonyl benzthiazolium p-toluene sulphonate and tetra- or pentaazaindenes especially those substituted by hydroxyl or amino groups e.g. those described by Birr, Z. Wiss. Phot. 47, 2–58 (1952). A very effective azaindene emulsion stabilizer is 5-methyl-7-hydroxy-s-triazolo[1,5-a] pyrimidine which can be used together with other emulsion stabilizers e.g. those of the type described above.

The emulsions may be X-ray and other non-spectrally sensitized emulsions as well as orthochromatic, panchromatic or infrared-sensitive emulsions. The emulsions may be spectrally sensitized by means of neutrocyanines, carboxycyanines, rhodacyanines, hemicyanines, merocyanines, oxonol dyes, styryl dyes and the like as described by F. M. Hamer in "The cyanine dyes and related compounds" (1954).

The emulsions may further comprise other compounds that sensitize the emulsion by development acceleration e.g. alkylene oxide polymers. These alkylene oxide polymers may be of various type e.g. polyethylene glycol having a molecular weight of 1500 or more, alkylene oxide condensation products or polymers as described in U.S. Pat. Nos. 1,970,578, 2,240,472, 2,423,549, 2,441,389, 2,531,832 and 2,533,990 and in United Kingdom Patent Specifications Nos. 920,637, 940,051, 945,340, 991,608 and 1,015,023. These development accelerating compounds may also be present in the silver halide developing solution. Other development accelerating compounds are onium and polyonium compounds preferably of the ammonium, phosphonium and sulphonium type.

Other addenda e.g. hardening agents such as formaldehyde, mucochloric and mucobromic acid, dialdehydes, etc, wetting agents, plasticizers, matting agents, e.g. polymethyl methacrylate and silica particles, light-screening dyes, etc., may be present in the silver halide emulsion or another layer of the light-sensitive materials used according to the invention.

The compounds of the above general formula may be used in developers for various kinds of photographic silver halide elements e.g. black-and-white emulsions which include X-ray and lith emulsions and colour emulsions. They may be used in the silver complex diffusion transfer process and in addition to being useful for negative processing they may also be used for reversal processing. In reversal processing where after a first black-and-white development residual silver halide is rendered developable by uniform reexposure or by a chemical treatment and then developed by a second development which may be black-and-white or colour, the compounds of the invention are preferably used in the second developer so that development of the residual silver halide rendered developable is activated and thus maximum density is increased.

The compounds of the above general formula have been found particularly useful for the development, especially reversal development, of photographic colour elements. They can be used for the production of multicolour images as well as for the production of monochromic images e.g. monochromic radiographic dye images according to the technique described in U.S. Patent No. 3,734,735 and U.S. patent application Ser. No. 210,566 (= published German Patent Application No. 2,165,193). They can also be used in colour diffusion transfer processes.

As is known in the art of silver halide colour photography, dyestuff images are formed by coupling of appropriate colour forming couplers with the oxidation products of aromatic primary amino colour developers particularly p-phenylene diamine colour developing agents. By the presence in the colour developers of the novel development accelerators, the maximum density of the dyestuff images as well as the contrast can be increased which results in improved colour saturation. Moreover, in addition to having a favourable development accelerating action, these compounds do not give rise to difficulties in the subsequent bleaching of the silver image as often occurs when using development accelerating onium compounds e.g. quaternary ammonium compounds.

In multilayer photographic elements used in colour photography for the reproduction of multicolour images there are generally three selectively sensitive emulsion layers (each of which may consist of several strata finished to different speed levels) coated on the same side of a photographic support, such as film or paper. Such multilayer elements can also have other layers for special purposes including gelatin or other subbing layers, antihalation layers, protective coatings, etc.

The three selectively sensitive emulsion layers are a blue-sensitive emulsion layer, an emulsion layer sensitized to the green region of the spectrum and an emulsion layer sensitized to the red region of the spectrum. In as much as many photographic silver halide emulsions have an inherent blue sensitivity, the photographic elements generally have a yellow filterlayer beneath the blue-sensitive uppermost emulsion layer for the purpose of absorbing substantially all blue radiation which would otherwise be transmitted to the green- and red-sensitized emulsion layers.

The invention is primarily concerned with colour development wherein the colour-forming couplers are within the silver halide emulsions. However, colour development may also be of the type well known in the art wherein the colour forming couplers are within the colour developer.

The colour-forming couplers are of the customary types employed in colour photography : pyrazolone couplers for formation of the magenta image, phenolic or naphtholic couplers for formation of the cyan image and open-chain compounds containing a reactive methylene group for formation of the yellow image.

When the multicolour elements have incorporated colour couplers the blue-sensitive emulsion layer comprises the yellow-forming colour coupler, the green-sensitized emulsion layer comprises the magenta-forming colour coupler and the red-sensitized emulsion layer comprises the cyan-forming colour coupler.

For the incorporation of the colour forming couplers in the silver halide emulsions, the conventional methods can be applied, e.g. they can be incorporated from solutions in high-boiling sparingly water-miscible solvents such as di-n-butyl phthalate and tricresyl phosphate or in low-boiling sparingly water-miscible solvents such as ethyl acetate, methylene chloride and chloroform, etc. or mixtures of both types of solvents. For this purpose these solutions are dispersed in extremely fine droplets, preferably in the presence of a wetting or dispersing agent into the hydrophilic colloid medium, the low-boiling sparingly water-miscible solvent then being removed by evaporation. Of course other techniques known by those skilled in the art for incorporating colour couplers, into colloid compositions can be used. For instance, the water-soluble colour couplers i.e. those containing a water-solubilizing sulpho group, in acid or salt form, can be incorporated into the coating composition of the layer in question from an aqueous or alkaline solution.

The hydrophilic colloid composition into which the colour couplers are dispersed or dissolved need not necessarily be the coating composition itself of the silver halide emulsion layer into which the colour couplers are intended to be present. The compounds may advantageously be first dispersed or dissolved in an aqueous non-light-sensitive hydrophilic colloid solution whereupon the resultant mixture after the occasional removal of the organic solvents employed, is intimately mixed with the said coating composition of the light-sensitive silver halide emulsion layer just before coating.

For more details about particularly suitable techniques that may be employed for incorporating colour couplers into a silver halide emulsion layer of a photographic material there can be referred to e.g. U.S. Pat. Nos. 2,269,158; 2,284,887; 2,304,939; 2,304,904 and 2,322,027, United Kingdom Patent Specification Nos. 791,219; 1,098,594; 1,099,414; 1,099,415; 1,099,416 and 1,099,417, French Patent Specification No. 1,555,663, Belgian Patent Specification No. 722,026, German Patent Specification No. 1,127,714 and to United Kingdom Patent Application No. 14,763/69.

In the colour development aromatic primary amino developing substances are used, which are capable of forming azomethine dyes by coupling in their oxidized form with the colour-forming couplers. Suitable developing agents are more particularly p-phenylene diamine and derivatives thereof e.g. N,N-dialkyl-p-phenylene diamines, N,N-dialkyl-N'-sulphomethyl-p-phenylenediamine, N,N-dialkyl-N'-carboxymethyl-p-phenylenediamine, the sulphonamido substituted p-phenylene diamines disclosed in U.S. Pat. No. 2,548,574 and other substituted p-phenylene diamines disclosed in U.S. Pat. No. 2,566,271.

Typical examples of p-phenylenediamines are N,N-diethyl p-phenylene diamine, 2-amino-5-diethylaminotoluene, N-butyl-N-sulphobutyl-p-phenylene diamine, 2-amino-5-[N-ethyl-N($\beta$-methylsulphonamido)ethyl]aminotoluene, N-ethyl-N-$\beta$-hydroxyethyl-p-phenylenediamine, etc. These developing agents are used usually in their salt form such as the hydrochloride or sulphate.

The following example illustrates the present invention.

EXAMPLE

Strips of a conventional multicolour reversal film material having incorporated colour couplers for the cyan, magenta and yellow separation images were exposed through a grey continuous wedge to white light in a Herrnfeld Sensitometer.

The exposed strips were then processed as follows:
treatment for 10 seconds at 25° C in a pre-bath of the following composition:

| water | 800 ml |
|---|---|
| ethylene diamine tetraacetic acid tetrasodium salt | 2 g |
| anhydrous sodium sulphate | 100 g |
| borax | 15 g |
| water to make | (pH 9.30) | rinsing for 15 seconds and brushing of the back to remove antihalation layer;

developing for 3 min. 45 sec. at 25° C in a black-and-white developer of the following composition:

| N-methyl-p-aminophenol sulphate | 3 g |
|---|---|
| hydroquinone | 6 g |
| sodium metabisulphite | 0.5 g |
| sodium hexametaphosphate | 2 g |
| sodium sulphite | 50 g |
| anhydrous sodium carbonate | 40 g |
| potassium bromide | 2.3 g |
| potassium thiocyanate | 2.5 g |
| potassium iodide | 6 mg |
| water to make | 1000 ml |
| | (pH 10.2) | treatment for 2 minutes in a stop bath of the following composition:

| potassium alum | 15 g |
|---|---|
| boric acid | 6 g |
| sodium hydrogen diacetate | 15 g |
| sodium metabisulphite | 1 g |
| water to make | 1000 ml |
| | (pH 4.2) | rinsing with water for 3 minutes and overall re-exposing the material for 1 minute at 25° C;
colour developing for 4 minutes at 25° C in a colour developer of the following composition:

| sodium hexametaphosphate | 1 g |
|---|---|
| sodium sulphite | 4 g |
| anhydrous sodium carbonate | 25 g |
| potassium bromide | 2.2 g |
| sodium hydroxide | 0.6 g |
| hydroxylamine hydrochloride | 1.2 g |
| N,N-diethyl-p-phenylene diamine hydrochloride | 2.7 g |
| potassium iodide | 4 mg |
| development activator as listed in the table hereinafter | 250 mg |
| water to make | 1000 ml |
| | (pH 10.7) | rinsing with water for 10 sec. at 25° C;
fixing for 3 minutes at 25° C in the following fixing solution:

| potassium alum | 15 g |
|---|---|
| acid sodium sulphate | 13 g |
| sodium acetate trihydrate | 25 g |
| sodium bisulphite | 12 g |
| sodium thiosulphate | 200 g |
| water to make | 1000 ml |
| | (pH 3.9) | rinsing with water for 2 min. at 25° C;
silver bleaching for 4 min. at 25° C in the following bleach bath:

| potassium bromide | 15 g |
|---|---|
| potassium alum | 45 g |
| acid potassium sulphate | 2 g |
| sodium acetate trihydrate | 5 g |
| sodium hydrogen diacetate | 10 g |
| potassium hexacyanoferrate(III) | 75 g |
| water to make | 1000 ml |
| | (pH 3.9) | rinsing with water for 3 min. at 25° C;
treating for 3 min. at 25° C in the above fixing solution;
rinsing with water for 5 min. at 25° C, and stabilizing for 8 sec. at 25° C in a stabilizing bath comprising per liter 13 ml of a 40% aqueous formaldehyde solution and a wetting agent.

In the following table the values are given which were obtained for minimum and maximum density and for the average gradient of the characteristic curves measured over an exposure range of $\Delta \log It = 0.60$ beginning at the point corresponding to density 0.70 above fog.

Table

| development activator | $D_{min}$ blue | green | red | $D_{max}$ blue | green | red | Gradient blue | green | red |
| --- | --- | --- | --- | --- | --- | --- | --- | --- | --- |
| none | 0.23 | 0.15 0.14 | | 1.69 | 1.75 | 1.50 | 0.86 | 0.91 | 1.07 |
| compound of preparation 1 | 0.20 | 0.14 | 0.14 | 1.84 | 1.87 | 1.87 | 1.13 | 1.08 | 1.28 |
| compound of preparation 3 | 0.20 | 0.14 | 0.14 | 1.89 | 1.88 | 1.87 | 1.16 | 1.15 | 1.34 |
| compound of preparation 6 | 0.21 | 0.13 | 0.13 | 2.59 | 2.62 | 2.42 | 1.70 | 1.61 | 1.70 |
| compound of preparation 7 | 0.23 | 0.14 | 0.14 | 2.92 | 2.72 | 2.65 | 2.21 | 1.69 | 1.98 |

The above results show that when colour development takes place in the presence of a compound according to the present invention, higher contrast and higher maximum density are obtained. The selectivity of colour reproduction is also favourable.

We claim:

1. A method of developing a photographic silver halide element containing imagewise developable silver halide by means of a silver halide developing solution wherein the developing solution contains a derivative of a polyethylene glycol or a $C_1$-$C_5$ monoalkyl ether thereof corresponding to the formula:

$$R_1O(CH_2CH_2O)_nX-A-Y-R_2$$

wherein
  $R_1$ is hydrogen, $C_1$-$C_5$ alkyl or the group $X-A-Y-R_2$
  $n$ is an integer of at least 4
  X is CO, $SO_2$, CONH or, when $R_1$ is $X-A-Y-R_2$ may be a chemical monovalent bond,
  A is alkylene or arylene,
  Y is a sulphur or selenium atom, and
  $R_2$ is an alkyl group.

2. Method according to claim 1, wherein the derivative is present in the developing solution in an amount comprised between about 50 mg and 10 g per liter.

3. Method according to claim 1, wherein the developable silver halide has been formed by uniform reexposure of the previously image-wise exposed and black-and-white developed photographic element.

4. Method according to claim 1, wherein the development is a colour development by means of a colour developing composition.

5. Method according to claim 1, wherein the photographic element is a colour element of the type having incorporated colour couplers capable of coupling with the oxidation products of a colour developing agent to form dyestuff images.

6. Method according to claim 5, wherein the photographic colour element is a multicolour element comprising at least one blue-sensitive emulsion layer with yellow-forming colour coupler, at least one green-sensitized emulsion layer with magenta-forming colour coupler and at least one red-sensitized emulsion layer with cyan-forming colour coupler.

7. A photographic developer comprising a silver halide developing agent and a derivative of a polyethylene glycol or a mono $C_1$-$C_5$ alkylether thereof corresponding to the formula:

$$R_1O(CH_2CH_2O)_nX-A-Y-R_2$$

wherein
  $R_1$ is hydrogen, $C_1$-$C_5$ alkyl or the group $X-A-Y-R_2$
  $n$ is an integer of at least 4
  X is CO, $SO_2$, CONH or, when $R_1$ is $X-A-Y-R_2$ may be a chemical monovalent bond,
  A is alkylene or arylene,
  Y is a sulphur or selenium atom, and
  $R_2$ is an alkyl group.

8. A photographic developer according to claim 7, wherein the derivative is present in an amount comprised between about 50 mg and about 10 g per liter.

9. A photographic developer according to claim 7, wherein the developing agent is an aromatic primary amino colour developing agent.

10. A photographic developer according to claim 9, wherein the developing agent is a p-phenylene diamine colour developing agent.

* * * * *

UNITED STATES PATENT AND TRADEMARK OFFICE
CERTIFICATE OF CORRECTION

PATENT NO. : 4,038,075
DATED : July 26, 1977
INVENTOR(S) : Robert Joseph POLLET ET AL It is certified that error appears in the above-identified patent and that said Letters Patent are hereby corrected as shown below:

Column 1, line 7, "thest" should read -- these --;
Column 3, line 38, "hous" should read -- hours --;
Column 7, line 20, "2,304,904" should read -- 2,304,940 --;
Column 7, line 65, in the composition, "water to make     (pH 9.30)" should read -- water to make     1000ml
(pH 9.30) --;
Column 9, claim 1, line 32, "contains a derivative" should read
-- contains a silver halide developing agent and a derivative --.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*